US00PP34008P2

(12) United States Plant Patent
Whitaker

(10) Patent No.: US PP34,008 P2
(45) Date of Patent: Mar. 15, 2022

(54) STRAWBERRY PLANT NAMED 'FL 17.15-86'

(50) Latin Name: ***Fragaria* X *ananassa* Duchesne**
Varietal Denomination: FL 17.15-86

(71) Applicant: Florida Foundation Seed Producers, Inc., Marianna, FL (US)

(72) Inventor: Vance M. Whitaker, Brandon, FL (US)

(73) Assignee: FLORIDA FOUNDATION SEED PRODUCERS, INC., Marianna, FL (US)

( * ) Notice: Subject to any disclaimer, the term of this patent is extended or adjusted under 35 U.S.C. 154(b) by 0 days.

(21) Appl. No.: 17/243,840

(22) Filed: Apr. 29, 2021

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./156, 208, 209
See application file for complete search history.

(56) References Cited

U.S. PATENT DOCUMENTS

| | | | |
|---|---|---|---|
| PP25,574 | P3 | 5/2015 | Whitaker |
| PP30,385 | P3 | 4/2019 | Whitaker |
| PP30,564 | P3 | 6/2019 | Whitaker |

*Primary Examiner* — Susan McCormick Ewoldt
*Assistant Examiner* — Karen M Redden
(74) *Attorney, Agent, or Firm* — Dentons US LLP

(57) ABSTRACT

A new and distinct variety of strawberry (*Fragaria* X *ananassa*), which originated from seed produced by a hand-pollinated cross between 'FL 14.76-75' and 'Florida Beauty'. The new strawberry, named 'FL 17.15-86', can be distinguished at least by its consistently well-shaped conical fruit; even medium-red fruit color; and fruit with intense flavor due to both high soluble solids content and high titratable acidity when grown in West Central Florida or other regions that have a climate similar to that of West Central Florida.

1 Drawing Sheet

Latin name of the genus and species of the plant claimed: *Fragaria* X *ananassa* Duchesne.

Variety denomination: 'FL 17.15-86'.

BACKGROUND OF THE INVENTION

The present invention relates to a new and distinct variety of strawberry plant (*Fragaria* X *ananassa* Duchesne) named 'FL 17.15-86'. This new strawberry plant is distinguished at least by its ability to produce fruit that have consistent conical shape and intense flavor when grown in West Central Florida. Asexual propagation of 'FL 17.15-86' was performed at Balm, Fla., which is also where the selection was made and where plants were tested. 'FL 17.15-86' can be contrasted with 'Florida Brilliance' (U.S. Plant Pat. No. 30,564) and 'Florida127' (U.S. Plant Pat. No. 25,574), which are the current, dominant strawberry varieties in Hillsborough County, Fla. 'FL 17.15-86' is a promising candidate for commercial success because it produces firm, evenly colored, and consistently shaped fruit with intense flavor.

SUMMARY OF THE INVENTION

'FL 17.15-86', when grown in a subtropical climate during the fall, winter, or a combination thereof, can be distinguished from all other strawberry plants by at least the following characteristics: consistently well-shaped conical fruit; even medium-red fruit color; and fruit with intense flavor due to both high soluble solids content and high titratable acidity.

'FL 17.15-86' originated in a strawberry breeding plot in Balm, Fla. The seed parent was 'FL 14.76-75', an unreleased, unpatented breeding selection with excellent fruit size and yield. The pollen parent was 'Florida Beauty' (U.S. Plant Pat. No. 30,385), released in 2016, with excellent fruit flavor, shape and color. The seeds resulting from the controlled hybridization were germinated in a greenhouse, and the resulting seedlings were planted and allowed to produce daughter plants by asexual propagation (i.e. by runners). Two daughter plants from each seedling were transplanted to raised beds, where they fruited. 'FL 17.15-86' was selection number 86 of the 15$^{th}$ cross in the 2017-2018 seedling trial, and thus was given the breeding trial designation of 'FL 17.15-86'. 'FL 17.15-86' exhibited high yields of consistently shaped fruit with even, attractive color and intense flavor. 'FL 17.15-86' has been asexually propagated annually by runners; and test plantings have established that the vegetative and fruit characteristics of the propagules are identical to those of the initial daughter plants.

'FL 17.15-86' can be distinguished from its seed parent 'FL 14.76-75' at least by its more intense fruit flavor and more consistent conical shape. 'FL 17.15-86' is believed to be phenotypically most similar to its pollen parent. Nonetheless, 'FL 17.15-86' can also be distinguished from its pollen parent 'Florida Beauty' at least by its greater fruit size and yield.

Currently, 'Florida Brilliance' (U.S. Plant Pat. No. 30,564) and 'Florida127' (U.S. Plant Pat. No. 25,574), are the two dominant strawberries varieties in Hillsborough County, Fla. 'FL 17.15-86' has similar fruit size to 'Florida Brilliance' (Table 1), but with higher soluble solids content and titratable acidity than 'Florida Brilliance' (Table 2). 'FL 17.15-86' has smaller fruit size than 'Florida127' and similar soluble solids content to 'Florida127'. However, the fruit of 'FL 17.15-86' is more consistently conical in shape than 'Florida127' and higher acidity (Table 2).

'FL 17.15-86' is less susceptible to Phytophthora root and crown rots (caused by *Phytophthora cactorum*) than both commercial standards but is more susceptible to charcoal rot (caused by *Macrophomina phaseolina*) than both commercial standards.

BRIEF DESCRIPTION OF THE DRAWINGS

'FL 17.15-86' is illustrated by the accompanying photograph that shows fruit from a 5 month-old specimen. The colors shown are as true as can be reasonably captured by conventional photographic procedures. The photograph was captured in March of 2020 in West Central Florida.

FIG. 1. Shows fruit from a 5-month-old plant at varying stages of ripeness.

DETAILED BOTANICAL DESCRIPTION

The following detailed botanical description sets forth the distinctive characteristics of 'FL 17.15-86'. The present botanical description is of 'FL 17.15-86' when grown under the ecological conditions that prevail during the winter production season in Balm, Fla., i.e., warm days and cool nights. Colors are objectively described using the the CIELAB color scale (originally published by the International Commission on Illumination (CIE) in 1976) as measured using a Minolta Chroma Meter CR-400 (Minolta, Ramsey, N.J.) colorimeter with a 1 cm aperture, calibrated against a white tile (Y=85.5, x=0.3164, y=0.3237). When the CIELAB color designations differ from the accompanying photographs, the CIELAB color designations are accurate.

Phenotypic Description of *Fragaria* X *ananassa* Duchesne 'FL 17.15-86'

Classification:
- *Botanical.*—*Fragaria*X *ananassa* Duchesne.
- *Common name.*—Strawberry.

Parentage:
- *Seed parent.*—'FL 14.76-75'.
- *Pollen parent.*—'Florida Beauty'.

Plant:
- *Average height.*—15 cm to 20 cm.
- *Average width.*—20 cm to 25 cm.
- *Growth habit.*—Semi-upright.
- *Number of crowns per plant.*—5 to 9 depending on seasonal conditions.
- *Vigor.*—Medium.

Leaf:
- *Overall description.*—Pinnately compound with three leaflets.

Petiole:
- *Average length.*—10.7 cm.
- *Average diameter.*—4.0 mm.
- *Pubescence.*—Light.
- *Pubescence density.*—Sparse.
- *Pose of hairs.*—Perpendicular.
- *Texture.*—Smooth.
- *Anthocyanin presence.*—Occasional.
- *Color.*—Light green (L*=59.07, a*=−16.17, b*=34.40).

Petiolule:
- *Length.*—Terminal leaflet: 7.5 mm. Lateral leaflets: 3.2 mm.
- *Diameter.*—1.7-1.8 mm.
- *Color.*—Light green (L*=48.27, a*=−12.21, b*=29.27).

Stipule:
- *Length.*—33 mm to 35 mm.
- *Width.*—21-24 mm along the base of the petiole attachment.
- *Anthocyanin presence.*—Absent.
- *Color.*—Light green (L*=67.22, a*=−5.94, b*=27.26).

Terminal leaflet:
- *Average length.*—68 mm.
- *Average breadth.*—61 mm.
- *Length/width ratio.*—1.11.
- *Shape in cross section.*—Slightly concave.
- *Color, upper surface.*—Medium-light green (L*=38.54, a*=−14.98, b*=20.55).
- *Color, lower surface.*—Light green (L*=52.75, a*=−4.60, b*=21.44).
- *Glossiness.*—Slight gloss.
- *Base shape.*—Cuneate.
- *Apex descriptor.*—Rounded.
- *Pubescence density.*—Sparse to moderate.
- *Texture.*—Moderately smooth.
- *Venation pattern.*—Pinnate.

Secondary leaflets:
- *Average length.*—66 mm.
- *Average breadth.*—62 mm.
- *Length/width ratio.*—1.06.
- *Shape in cross section.*—Slightly concave.
- *Color, upper surface.*—Medium-light green (L*=36.30, a*=−13.57, b*=17.15).
- *Color, lower surface.*—Light green (L*=52.35, a*=−4.58, b*=20.77).
- *Glossiness.*—Slight gloss.
- *Base shape.*—Oblique rounded.
- *Apex descriptor.*—Obtuse.
- *Pubescence density.*—Sparse to moderate.
- *Texture.*—Moderately smooth.
- *Venation pattern.*—Pinnate.

Leaflet margins: Crenate, with an average of 22 and 23 serrations per terminal and secondary leaflet, respectively.

Stolons:
- *Number of daughter plants.*—20 to 45 depending on environmental conditions.
- *Anthocyanin presence.*—Occasional.
- *Thickness.*—2 mm to 3 mm.
- *Pubescence.*—Light with pose of hairs ascending.

Inflorescence:
- *Time of flowering.*—Partial remontancy, commencing two weeks after establishment and continually thereafter in suitable climate.
- *Flower number per plant.*—45 to 60 flowers over a 4 month Florida growing season.
- *Flower height.*—0 to 20 cm above soil surface depending on angle of pedicel.
- *Position relative to canopy.*—Flowers open at or slightly below canopy height.
- *Branching of the inflorescence.*—At or very close to the crown.

Petals:
- *Number.*—5 to 6.
- *Length.*—12 to 13 mm.
- *Width.*—11 to 13 mm.

*Shape*.—Orbicular.
*Apex*.—Rounded.
*Base*.—Rounded.
*Margin*.—Smooth.
*Average diameter of the corolla* (*i.e. the petals collectively*).—33 mm.
*Average number of stamens*.—25.
*Color, upper surface*.—White (L*=83.96, a*=−2.09, b*=7.65).
*Color, lower surface*.—White (L*=83.93, a*=−2.03, b*=7.83).

Calyx:
*Diameter*.—30-36 mm.
*Diameter of calyx relative to corolla*.—0% greater in diameter.
*Diameter of calyx relative to the fruit*.—0% greater in diameter.
*Insertion of calyx*.—Level to slightly inserted.
*Color*.—Medium-light green (L*=49.46, a*=−18.97, b*=29.63).

Sepals:
*Number per flower*.—10-12.
*Length*.—12-15 mm.
*Width*.—7-10 mm.
*Apex*.—Subacute to lobed.
*Margin*.—Smooth.
*Color, upper surface*.—Medium green (L*=47.16, a*=−14.23, b*=22.64).
*Color, lower surface*.—Light green (L*=38.75, a*=−16.08, b*=22.89).

Pedicels: Attached to mature primary fruit and 10 cm to 14 cm in length and 3 to 4 mm in diameter depending on the time of the season. At peak production, the plant will have several crowns, each producing a truss. Each truss will have 5 to 8 pedicels. Inflorescences branch very close to the crown, rendering the peduncle rarely visible.

Fruit:
*Number per truss*.—5 to 8.
*Shape*.—Medium conical to cordate.
*Average fruit weight*.—20 to 24 g (Table 1).
*Weight, primary fruit*.—25 to 40 g.
*Weight, secondary and tertiary fruit*.—14 to 22 g.
*Length, primary fruit*.—45 to 55 mm.
*Width, primary fruit*.—34 to 40 mm.
*Fruit flavor*.—Similar sweetness 'Florida127' which is the current commercial flavor standard, but with higher acidity.
*Fruit soluble solids content* (*brix*).—As high as 9.25% in March 2020 (Table 2).
*Fruit firmness*.—Similar to commercial standard 'Florida Brilliance'.
*Fruit cavity*.—Rare.
*Achenes*.—Slightly sunken, 120 to 260 per fruit.
*External fruit color*.—Glossy medium to dark red (a*=41.08).
*Internal fruit color*.—Medium red (a*=25.86).
*Evenness of color*.—Very consistently even.
*Flesh and skin firmness at full ripe stage*.—Very firm.
*Rain damage*.—Similar to 'Florida Brilliance'.

Early yield: Slightly less than 'Florida Brilliance (Table 1).

Preferred planting period: October 15$^{th}$ to October 20$^{th}$ in West Central Florida.

Nursery performance: 'FL 17.15-86' produces slightly more runners than the commercial standards.

Disease resistance:
*Phytophthora crown rot* (*caused by Phytophthora cactorum*).—Moderately resistant.
*Powdery mildew* (*caused by Podosphaera aphanis*).—Moderately susceptible.
*Anthracnose fruit rot* (*caused by Colletotrichum acutatum*).—Moderately susceptible.
*Charcoal rot* (*caused by Macrophomina phaseolina*).—Susceptible.

TABLE 1

Performance of three strawberry genotypes during the 2019-20 season in Balm, Florida.

| | Marketable yield (g/plant) | | | | | | |
|---|---|---|---|---|---|---|---|
| Cultivar | November | December | January | February 2019-20 | March | Total | Wt/fruit (g)[z] |
| 'Florida Brilliance' | 4.3 b | 104.0 a | 180.7 b | 436.3 a | 180.7 a | 905.8 a | 22.4 b |
| 'Florida 127' | 8.3 a | 80.2 b | 259.8 a | 446.7 a | 141.3 b | 936.2 a | 27.3 a |
| 'FL 17.15-86' | 3.7 b | 89.8 b | 144.0 c | 401.2 a | 187.7 a | 825.8 b | 22.0 b |

[z]Mean fruit weight was determined by dividing total marketable fruit yield per plot by total marketable fruit number per plot.
[y]Mean separation within columns is by Tukey's HSD test, $P < 0.05$.

TABLE 2

Soluble solids content (SSC), pH, titratable acidity (TA) and SSC/TA from four harvests dates.

| Cultivar | SSC (%) | pH | TA (%) | SSC/TA |
|---|---|---|---|---|
| December 2019 | | | | |
| 'Florida Brilliance' | 6.41 b | 3.67 ab | 0.81 ab | 7.96 ab |
| 'Florida127' | 8.68 a | 3.82 a | 0.72 b | 12.13 a |
| 'FL 17.15-86' | 7.59 ab | 3.51 b | 1.08 a | 7.06 b |
| January 2020 | | | | |
| 'Florida Brilliance' | 8.43 a | 3.67 a | 0.82 a | 10.56 a |
| 'Florida127' | 9.09 a | 3.63 a | 0.86 a | 10.54 a |
| 'FL 17.15-86' | 9.18 a | 3.60 a | 0.92 a | 9.94 a |
| February 2020 | | | | |
| 'Florida Brilliance' | 6.14 b | 3.76 a | 0.56 b | 10.87 ab |
| 'Florida127' | 7.62 a | 3.75 a | 0.61 b | 12.56 a |
| 'FL 17.15-86' | 6.96 ab | 3.62 a | 0.74 a | 9.39 b |
| March 2020 | | | | |
| 'Florida Brilliance' | 8.28 b | 3.63 a | 0.82 b | 10.09 ab |
| 'Florida127' | 9.63 a | 3.73 a | 0.78 b | 12.34 a |
| 'FL 17.15-86' | 9.25 a | 3.53 b | 1.01 a | 9.16 b |

[z]Mean separations within harvest dates and columns are by Tukey's HSD test, $P \leq 0.05$

What is claimed is:

1. A new and distinct strawberry plant named 'FL 17.15-86' as illustrated and described herein.

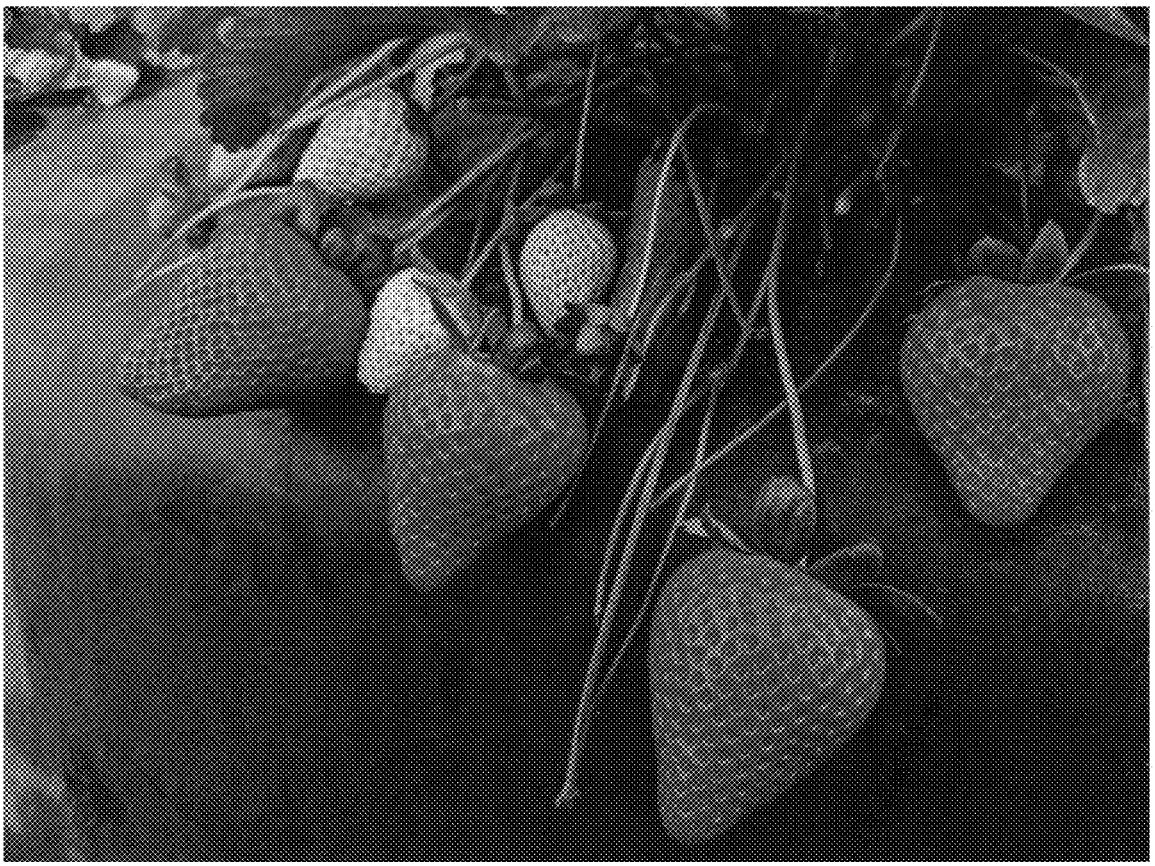

* * * * *